United States Patent
Stahl et al.

(10) Patent No.: US 12,162,828 B2
(45) Date of Patent: Dec. 10, 2024

(54) PROCESS FOR PREPARING 3-HYDROXY-3-METHYLBUTYRIC ACID (HMB) AND SALTS THEREOF

(71) Applicant: EVONIK OPERATIONS GMBH, Essen (DE)

(72) Inventors: Timo Stahl, Limeshain (DE); Axel Ronneburg, Hanau (DE); Imad Moussallem, Hanau (DE); Juliette Halli, Frankfurt am Main (DE); Petra Picha, Friedrichsdorf (DE)

(73) Assignee: Evonik Operations GmbH, Essen (DE)

( * ) Notice: Subject to any disclaimer, the term of this patent is extended or adjusted under 35 U.S.C. 154(b) by 575 days.

(21) Appl. No.: 17/600,289

(22) PCT Filed: Mar. 25, 2020

(86) PCT No.: PCT/EP2020/058340
§ 371 (c)(1),
(2) Date: Sep. 30, 2021

(87) PCT Pub. No.: WO2020/200952
PCT Pub. Date: Oct. 8, 2020

(65) Prior Publication Data
US 2022/0204435 A1   Jun. 30, 2022

(30) Foreign Application Priority Data
Apr. 2, 2019 (EP) .................................. 19166808

(51) Int. Cl.
*C07C 51/08* (2006.01)
*C07D 301/12* (2006.01)

(52) U.S. Cl.
CPC ............ *C07C 51/08* (2013.01); *C07D 301/12* (2013.01)

(58) Field of Classification Search
CPC .............................. C07C 51/08; C07D 301/12
See application file for complete search history.

(56) References Cited

U.S. PATENT DOCUMENTS

| | | | |
|---|---|---|---|
| 5,087,472 A | * | 2/1992 | Nissen .................. A23K 50/10 |
| | | | 514/557 |
| 8,809,576 B2 | | 8/2014 | Schraven |
| 2010/0179112 A1 | | 7/2010 | Rathmacher |
| 2010/0210871 A1 | | 8/2010 | Kobler |
| 2011/0130540 A1 | | 6/2011 | Cirakovic |
| 2014/0256980 A1 | | 9/2014 | Yao-En |

FOREIGN PATENT DOCUMENTS

| | | | |
|---|---|---|---|
| BE | 1001038 | 6/1989 | |
| JP | H 10276792 | * 10/1998 | ................ C12P 7/42 |

OTHER PUBLICATIONS

Ohno, et al., Ring opening of epoxides with acetone cyanohydrin catalyzed by lanthanoid (III) alkoxides, Chemistry Letters, pp. 975-978 (Year: 1993).*
International Preliminary Report on Patentability for corresponding intenational application PCT/EP2020/058340, filed Mar. 25, 2020.
International Search Report for corresponding intenational application PCT/EP2020/058340, filed Mar. 25, 2020.
Written Opinion of the International Searching Authority for corresponding intenational application PCT/EP2020/058340, filed Mar. 25, 2020.
European Search Report for corresponding EP 19 16 6808, filed Apr. 2, 2019.
Ohno, et al., "Ring Opening of Epoxides with Acetone Cyanohydrin Catalyzed by Lanthanoid(III) Alkoxides," *Chemistry Letters* 6:975-978 (Jan. 1993).

* cited by examiner

*Primary Examiner* — Yate' K Cutliff
(74) *Attorney, Agent, or Firm* — Law Office of Michael A. Sanzo, LLC

(57) ABSTRACT

The present invention pertains to a process for preparing 3-hydroxy-3-methylbutyric acid (HMB) or a salt thereof, the method comprising (a) reacting isobutylene oxide with cyanide in order to obtain 3-hydroxy-3-methylbutyronitrile, and (b) hydrolyzing the 3-hydroxy-3-methylbutyronitrile obtained in step (a) in order to obtain HMB, wherein hydrolysis step (b) is performed using either at least one nitrilase enzyme or, alternatively, using a combination of enzymes, said combination comprising at least one nitrile hydratase and at least one amidase.

20 Claims, No Drawings

PROCESS FOR PREPARING 3-HYDROXY-3-METHYLBUTYRIC ACID (HMB) AND SALTS THEREOF

CROSS REFERENCE TO RELATED APPLICATIONS

The present application is US national stage of international application PCT/EP2020/058340, which has an international filing date of Mar. 25, 2020, and which was published on Oct. 8, 2020. The application claims priority to European application EP 19166808.6, filed on Apr. 2, 2019. The content of these prior applications is hereby incorporated by reference in its entirety.

FIELD OF THE INVENTION

The present invention pertains to a new process for preparing 3-hydroxy-3-methylbutyric acid (HMB) and salts of HMB.

BACKGROUND OF THE INVENTION

3-Hydroxy-3-methylbutyric acid (HMB) is known as a metabolite of the essential amino acid L-leucine. Due to its anabolic, anti-catabolic and lipolytic properties, HMB is used as a nutritional supplement for humans, in particular in strength— and endurance sports. In addition, HMB is used in pharmaceutical applications, such as in the treatment of muscular dystrophy.

The positive effects of HMB, however, are not limited to applications in humans. The use of HMB as feed additive or feed supplement has been described for a number of economically relevant livestock, such as poultry and pigs, see e.g. U.S. Pat. No. 5,087,472 or US 2010/0179112 A1.

The dosage form mainly applied for HMB is the calcium salt, which may be obtained from the free acid.

In the established manufacturing process, as described in EP 2 744 489 A1, the key synthetic reaction is sodium hypochloride (NaClO) oxidation of diacetone alcohol, whereby the HMB sodium salt is obtained. Neutralisation with hydrochloric acid yields HMB.

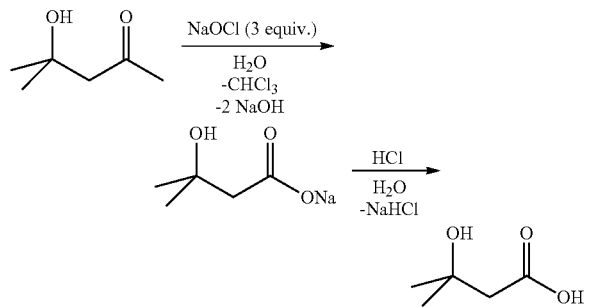

The established production process not only produces stoichiometric quantities of salt but also large quantities of undesirable hazardous substances such as chloroform. In addition, the yield of the oxidation reaction is rather low.

Accordingly, it was the objective of the present invention to provide a simple and inexpensive manufacturing process for HMB in which less hazardous byproducts are formed and in which the formation of byproducts is minimized, respectively.

SUMMARY OF THE INVENTION

The inventors have found a new synthesis route to HMB that meets the requirements of the above objective.

More specifically, the present invention provides a process for preparing 3-hydroxy-3-methylbutyric acid (HMB) or a salt thereof, the method comprising (a) reacting isobutylene oxide with cyanide in order to obtain 3-hydroxy-3-methylbutyronitrile, and (b) hydrolyzing the 3-hydroxy-3-methylbutyronitrile obtained in step (a) in order to obtain HMB, wherein hydrolysis step (b) is performed using either at least one nitrilase enzyme or, alternatively, using a combination of enzymes, said combination comprising at least one nitrile hydratase and at least one amidase.

DETAILED DESCRIPTION OF THE INVENTION

Key synthetic reaction of the process according to the invention is the reaction of isobutylene oxide (1,2-epoxy-2-methylpropane) with cyanide in aqueous solution at pH>7 (process step (a)).

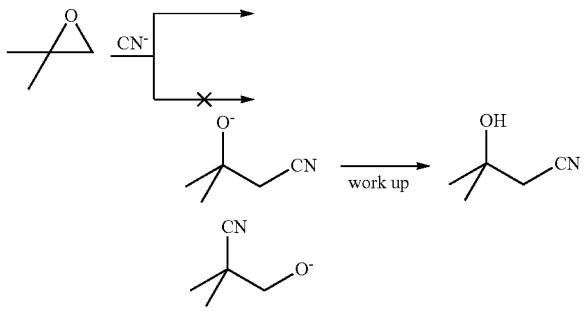

Surprisingly, it was found that the ring opening of the epoxide is completely selective in aqueous solution at pH>7, in particular between pH 7 and 12, meaning that the corresponding primary alcoholate is not formed at all. The reaction proceeds in a quantitative manner. 3-Hydroxy-3-methylbutyronitrile is obtained after aqueous, optionally slightly acidic, work-up from the alcoholate.

The selectivity of the above-mentioned ring-opening reaction is particularly surprising, as nucleophilic reactions with isobutene oxide generally results in the formation of the primary, terminal alcohol. Depending from the solvent system, the tertiary alcohol can be isolated as a small quantity product.

The ring-opening reaction according to the present invention can be carried out at room temperature. Alternatively, the reaction can be carried out at elevated temperature for accelerating the reaction. The amount of 1,2-epoxy-2-methylpropane relative to the amount cyanide should be between 1:1 and 1:1.2.

Typically, reaction times or residence times of from 10 min to 10 h and in particular 2 h to 5 h, will be appropriate for achieving reasonable and sufficient reaction yields.

The nitrile may be isolated from the reaction mixture and purified using techniques generally known in the art, e.g. distillation or flash chromatography on silica.

Suitable cyanides for the epoxide opening reaction are in particular alkali metal cyanides or alkaline earth metal cyanides. Preferably, sodium cyanide is used.

An aqueous sodium cyanide solution with a pH>7, in particular with a pH between 9 and 12, preferably with a pH of about 11, is particularly suitable.

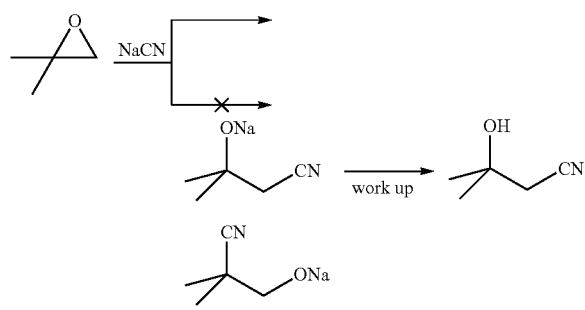

The isobutylene oxide used in step (a) may be obtained via catalytic epoxidation. Suitable oxidants for the process according to the present invention are hydrogen peroxide or hydroperoxides. Examples for hydroperoxides include tert-butyl hydroperoxide (tBuOOH, TBHP) and ethyl benzyl hydroperoxide (EBHP). As additional alternatives, the epoxidation step may be performed using ozone ($O_3$) or meta-chloroperoxybenzoic acid (mCPBA).

The preferred oxidant for the process according to the present invention is hydrogen peroxide ($H_2O_2$).

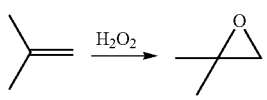

The amount of hydrogen peroxide relative to the amount of isobutene is not critical. Most suitable are molar ratios of isobutene:hydrogen peroxide from 100:1 to 1:10. Preferably, the molar ratio of isobutene to hydrogen peroxide is in the range of from 1:5 to 10:1. A molar ratio of isobutene to hydrogen peroxide of 1:2 is particularly preferred.

Besides the substrate and the oxidant or epoxidation reagent, a hetereogenous catalyst and a solvent is present in the reaction mixture.

The heterogeneous catalyst used for isobutylene oxide preparation according to the present invention contain a group 4 (e.g. Ti, Zr, HO, a group 5 (e.g. V, Nb, Ta) or a group 6 (e.g. Cr, Mo, W) metal and may be crystalline or amorphous. Preferably, the catalyst contains a group 4 metal, in particular titanium. Particularly preferred catalysts are crystalline molecular sieves, and particular zeolithes containing titanium.

The titanium silicalites useful as catalysts for the isobutene epoxidation include zeolithes, in which the titanium is substitutes for a portion of the silicon atoms in the lattice framework of a molecular sieve. Such substances are well-known in the art.

The titanium silicalites include the classes of molecular sieves commonly referred to as "TS-1" (having an MFI topology analogous to that of the ZSM-5 aluminosilicate zeolithes), "TS-2" (having an MEL topology analogous to that of the ZSM-11 aluminosilicate zeolithes) and "TS-3" (describes in BE 1,001,038). The preferred catalyst is titanium silicalite-1.

The amount of catalyst employed is not critical, but should be sufficient to accomplish the desired epoxidation in particularly short time. The optimal quantity of catalyst will depend on a number of factors including reaction temperature, isobutene concentration, hydrogen peroxide/epoxidation reagent concentration, type and concentration of organic solvent as well as catalyst activity and reactor type.

The catalyst may be used in powder, pellet, microspheric, extruded, monolithic or other suitable physical form.

The temperature applied for the epoxidation reaction is between 0° C. and 100° C., in particular between 30° C. and 80° C. and preferably between 35° C. and 40° C. The epoxidation reaction is generally performed at elevated pressure, as it is desirable to maintain the reaction components as a liquid mixture.

Typically, reaction times or residence times of from 10 min to 24 h and in particular 2 h to 5 h, will be appropriate for achieving reasonable and sufficient reaction yields.

The epoxide may be isolated from the reaction mixture and purified using techniques generally known in the art, e.g. vacuum distillation.

In a second process step (process step (b)), the 3-hydroxy-3-methylbutyronitrile obtained in step (a) is hydrolyzed to give HMB as a free acid.

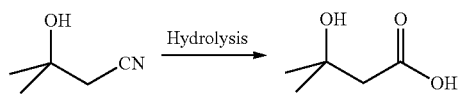

Nitriles can be readily converted to the corresponding carboxylic acids by a variety of chemical processes. Typical reagents are known in the art. For example, nitrile hydrolysis can be performed by reacting the nitrile with calcium hydroxide; ceroxide/zirconium oxide, optionally as nanopowder; acetone/potassium hydroxide; titanium dioxide, optionally in combination with sulfuric acid or in combination with sodium hydroxide or with potassium hydroxide/hydrogen peroxide.

Such processes however, typically require strongly acidic or caustic reaction conditions and/or high reaction temperatures. Further, unwanted byproducts and/or large amounts of inorganic salts are produced as unwanted waste.

With regard to process simplicity and product yield, it was surprisingly found that in comparison to the aforementioned chemical hydrolysis conditions, enzyme catalyzed hydrolysis provides superior results.

For enzyme catalyzed nitrile hydrolysis in aqueous solution, either a nitrilase enzyme or a combination of two enzymes, nitrile hydratase and amidase, can be used.

The nitrilase enzyme directly converts the aliphatic nitrile to the corresponding carboxylic acid, without formation of the corresponding amide intermediate.

The nitrile hydratase (NHase) initially converts the aliphatic nitrile to an amide, which can be subsequently further converted by the amidase to the corresponding carboxylic acid.

In the process according to the present invention, an enzyme having nitrilase activity, or, alternatively, a combination of enzymes having nitrilase activity is used.

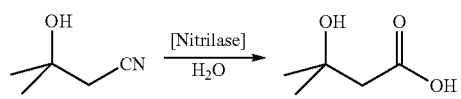

Enzyme catalyzed hydrolysis of 3-hydroxy-3-methylbutyronitrile is preferably performed in phosphate buffer (potassium dihydrogen phosphate/dipotassium hydrogen phosphate) at a pH in the range of 6.5 to 7.5 and at a Temperature in the range of 30° C. to 42° C.

The enzyme catalyst can be present in the form of microbial cells (biomass), such as *E. coli* cells, permeablized microbial cells, one or more cell components of a microbial cell extract or as (partially) purified enzymes. These different forms can be immobilized on a soluble or insoluble support.

In case the enzyme-catalyzed hydrolysis of 3-hydroxy-3-methylbutyronitrile is performed using microbial cells, it is possible to isolate the HMB product from the reaction medium by removing the bacterium biomass present in the medium to a complete extent (100%) or to a virtually complete extent, i.e. more than or greater than (>) 90%, >95%, >97%, >99%.

Alternatively, the remaining constituents of the reaction medium can be left in the HBM product to a large extent, i.e. to an extent of 30% to 100%, 40% to 100%, 50% to 100%, 60% to 100%, 70% to 100%, 80% to 100%, or 90% to 100%, preferably greater than or equal to ($\geq$) 50%, $\geq$60%, $\geq$70%, $\geq$80%, $\geq$90% or $\geq$95%, or else to a complete extent (100%). The latter variant, i.e. a mixture of HMB-product and biomass is particularly suitable for feed applications.

The biomass may removed or separated off by using separation methods such as, for example, centrifugation, filtration, decanting, flocculation or a combination thereof. Then, the biomass can be recycled, i.e. re-used in further nitrilase reactions.

The medium obtained after biomass-removal may then be thickened or concentrated using known methods such as, for example, with the aid of a rotary evaporator, thin-film evaporator, falling-film evaporator, by reverse osmosis, by nanofiltration or a combination thereof, to give the HMB product as lubricous fluid.

Free HMB has a strong odor. Therefore, livestock animals would avoid eating pure HMB. Accordingly, free HMB is only under certain conditions suitable as feed additive. However, HMB salts of alkali metals, alkaline earth metals or combinations thereof are free of odor and are converted into the free HMB acid in the animal stomach.

Accordingly, the HMB product obtained in step (b) may be converted to HMB salts including, but not limited to, alkali metal salts, alkaline earth metal salts, or both. In this case, HMB, in its free acid form, is treated with at least one source of cations, preferably of calcium cations, such as calcium hydroxide.

Optionally, the HMB salt, such as Ca-HMB, is recrystallized from a recrystallization solvent, such as ethanol, to provide crystalline HMB salt in high purity.

The HMB product, HMB or a HMB salt, can be used as feed, feed material, premix or feed additive.

Said feed, feed material, premix or feed additive may be prepared in a process comprising preparing 3-hydroxy-3-methylbutyric acid (HMB) or salt thereof according to a method of the present invention, as detailed above. The method for preparing the feed, feed material, premix or feed additive optionally further comprises the steps of
(e) admixing the HMB product or salt thereof with a processing aid, and/or
(f) pelletizing the HMB product or salt thereof, or the mixture obtained in step (e), and/or
(g) coating the HMB product or salt thereof, or the pellet obtained in step (f).

In the following, the invention is illustrated by non-limiting examples and exemplifying embodiments.

Examples

Material and Methods
Materials
　1,2-Epoxy-2-methylpropane (Aldrich)
　Natriumcyanide (Merck, p.A.)
　Potassium dihydrogenphosphate (Merck, p.A.)
　Dipotassium hydrogenphosphate (Roth, 98%)
　NIT59/NIT60 (Nitrilasekit c-LEcta)
HPLC
　Device: Agilent 1260 Infinity
　Column: RP18 Grace Alltima 5µ, 4.5 mm*250 mm
　Solvent: Gradient Acetonitril/1.5 Gew % aqueous phosphoric acid
　Detection: UV 229 nm
　Column temperature 20° C.
GC
GC for Isobutylene Oxide Analysis
　Device (GC, HPLC): Agilent (GC)
　Column: DB1701 (Agilent)
　Method: Injection-temp. 250° C., Detection temp. 250° C.,
　　Temperature programme: 40° C./5 min→10° C./min→125° C.→40° C./min→280° C.
　Retention times: Isobutene 1.99 min, Isobutene oxide 3.69 min, Methanol 2.55 min, side product 11.47 min
GC for Further Analysis
　Device: HP 6890 Series GC System
　Column: HP-5, 5% Phenyl Methyl Siloxane, length: 30 m, diameter: 320 µm
　Front Inlet Temperature 200° C.
　Detektion: FID @ 260° C.
　Carrier gas: He Synthesis of isobutylene oxide
(1,2-epoxy-2-methylpropane)

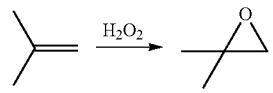

An autoclave with catalyst basket was charged with TS-1 catalyst (5.00 g, extrudate, Evonik). After a leak test with nitrogen, the pressure was released. MeOH was added via a pump. The temperature was slowly increased to 40° C. by means of a thermostat. Under rotation of the catalyst basket, a pressure of 2.0 bar (0.2 MPa) isobutylene was applied. As soon as pressure and temperature were constant, hydrogen peroxide (11.4 g, aqueous solution, 30% w/w) was added. After 150 min, an isobutylene conversion of 83% and the formation of the target product was determined by means of gas chromatographic analysis (reference measurement).

Synthesis of 3-hydroxy-3-methylbutyronitrile

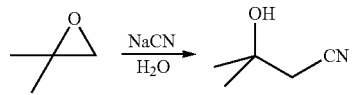

1,2-Epoxy-2-methylpropane (0.14 g, 1.9 mmol) was placed in a reaction vessel and dissolved in deionized water (5 mL). Under stirring, sodium cyanide (0.14 g, 2.0 mmol) was added. The resulting solution was stirred for 5 h at room temperature. Gaschromatographic analysis showed quantitative conversion (single peak at 13 min, for comparison of retention times see below). The above-referenced product was obtained from the sodium salt intermediate after hydrolysis.

GC retention times (for reference measurement).
1,2-Epoxy-2-methylpropane: 11 min
3-Hydroxy-3-methylbutyronitrile: 13 min
3-Hydroxy-2,2-dimethylpropionitrile 13.4 min Enzymatic hydrolysis of
3-hydroxy-3-methylbutyronitrile

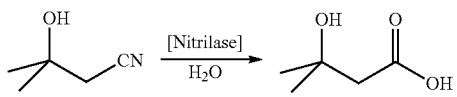

3-hydroxy-3-methylbutyronitrile (54 mg, 0.54 mmol) was placed in a reaction vessel and dissolved in phosphate buffer (5 mL, pH=7, potassium dihydrogen phosphate/dipotassium hydrogen phosphate). A sample of 500 μL of the thus-obtained solution was mixed with nitrilase solution (10 μL), NIT59 and NIT60 (c-LEcta, Leipzig), respectively.

The reaction mixture was shaken for 24 h at 37° C.

Product yields: Hydrolysis with enzyme NIT59: 20%; Hydrolysis with enzyme NIT60: 26%

The invention claimed is:

1. A process for preparing 3-hydroxy-3-methylbutyric acid (HMB) or a salt thereof, comprising:
    (a) reacting isobutylene oxide with cyanide in order to obtain 3-hydroxy-3-methylbutyronitrile; and
    (b) hydrolyzing the 3-hydroxy-3-methylbutyronitrile obtained in step (a) to obtain HMB;
    wherein hydrolysis step (b) is performed using either at least one nitrilase enzyme or, alternatively, using a combination of enzymes, said combination comprising at least one nitrile hydratase and at least one amidase.

2. The process of claim 1, wherein the cyanide used in process step (a) is an aqueous sodium cyanide solution with a pH>7.

3. The process of claim 1, wherein the cyanide used in process step (a) is in the form of an aqueous sodium cyanide solution with a pH of between 9 and 12.

4. The process of claim 1, wherein the amount of 1,2-epoxy-2-methylpropane relative to the amount cyanide is between 1:1 and 1:1.2.

5. The method of claim 1, wherein hydrolysis step (b) is performed using at least one enzyme having nitrilase activity.

6. The process of claim 5, wherein hydrolysis step (b) is performed in phosphate buffer at a pH in the range of 6.5 to 7.5 and at a temperature in the range of 37° C. to 42° C.

7. The process of claim 1, wherein hydrolysis step (b) is performed with the enzyme catalyst present in the form of microbial cells, in the form of permeabilized microbial cells, in the form of one or more cell components of a microbial cell extract or in the form of purified or partially purified enzymes.

8. The process of claim 1, wherein hydrolysis step (b) is performed with the enzyme catalyst present in the form of microbial cells.

9. The process of claim 8, wherein after step (b), the microbial cells are separated off and recycled.

10. The process of claim 1, further comprising:
    (c) converting the HMB product obtained in step (b) to HMB salts of alkali metals, alkaline earth metals or combinations thereof; and optionally
    (d) recrystallizing the HMB salt obtained in step (c).

11. The process of claim 10, wherein the HMB salt is calcium-HMB.

12. The process of claim 1, wherein the isobutylene oxide used in step (a) is obtained via catalytic epoxidation.

13. The process of claim 12, wherein the epoxidation is performed using hydrogen peroxide.

14. The process of claim 12, wherein the epoxidation is performed using a titanium silicalite catalyst.

15. The process of claim 10, wherein the amount of 1,2-epoxy-2-methylpropane relative to the amount cyanide is between 1:1 and 1:1.2.

16. The process of claim 15, wherein hydrolysis step (b) is performed using at least one enzyme having nitrilase activity.

17. The process of claim 16, wherein hydrolysis step (b) is performed with the enzyme catalyst present in the form of microbial cells, in the form of permeabilized microbial cells, in the form of one or more cell components of a microbial cell extract or in the form of purified or partially purified enzymes.

18. The process of claim 10, wherein the epoxidation is performed using a titanium silicalite catalyst.

19. The process of claim 18, wherein hydrolysis step (b) is performed using at least one enzyme having nitrilase activity.

20. A process for preparing feed, feed material or a premix of feed additive, comprising preparing 3-hydroxy-3-methylbutyric acid (HMB) or a salt thereof by the process of claim 1, and optionally further comprising:
    (e) admixing the HMB product or salt thereof with a processing aid; and/or
    (f) pelletizing the HMB product or salt thereof, or the mixture obtained in step (e); and/or
    (g) coating the HMB product or salt thereof, or the pellet obtained in step (f).

* * * * *